United States Patent
Morinaka et al.

(10) Patent No.: US 10,287,165 B2
(45) Date of Patent: *May 14, 2019

(54) IMIDIC ACID COMPOUND HAVING DIVALENT ANION AND PROCESS FOR PRODUCING THE SAME

(71) Applicant: CENTRAL GLASS CO., LTD., Ube-shi, Yamaguchi (JP)

(72) Inventors: Takayoshi Morinaka, Ube (JP); Makoto Kubo, Ube (JP); Wataru Kawabata, Ube (JP); Kenta Yamamoto, Saitama (JP); Takashi Mori, Ube (JP); Masutaka Shinmen, Sanyoonoda (JP); Hiroki Matsuzaki, Ube (JP); Ryosuke Kondo, Ube (JP); Mikihiro Takahashi, Ube (JP)

(73) Assignee: CENTRAL GLASS CO., LTD., Yamaguchi (JP)

( * ) Notice: Subject to any disclaimer, the term of this patent is extended or adjusted under 35 U.S.C. 154(b) by 35 days.

This patent is subject to a terminal disclaimer.

(21) Appl. No.: 15/529,638

(22) PCT Filed: Dec. 1, 2015

(86) PCT No.: PCT/JP2015/083795
§ 371 (c)(1),
(2) Date: May 25, 2017

(87) PCT Pub. No.: WO2016/088766
PCT Pub. Date: Jun. 9, 2016

(65) Prior Publication Data
US 2017/0267528 A1      Sep. 21, 2017

(30) Foreign Application Priority Data

Dec. 1, 2014 (JP) .................................. 2014-243291
Oct. 30, 2015 (JP) .................................. 2015-213824

(51) Int. Cl.
| | | |
|---|---|---|
| *C01B 21/086* | (2006.01) | |
| *C01B 21/097* | (2006.01) | |
| *H01M 10/0567* | (2010.01) | |
| *B01J 27/24* | (2006.01) | |
| *B01J 31/02* | (2006.01) | |
| *C07C 211/63* | (2006.01) | |
| *C07F 9/26* | (2006.01) | |

(Continued)

(52) U.S. Cl.
CPC ............ *C01B 21/097* (2013.01); *B01J 27/24* (2013.01); *B01J 31/0271* (2013.01); *C01B 21/086* (2013.01); *C01B 25/455* (2013.01); *C07C 211/63* (2013.01); *C07F 9/26* (2013.01); *C09K 3/16* (2013.01); *H01G 11/62* (2013.01); *H01M 6/166* (2013.01); *H01M 10/052* (2013.01); *H01M 10/054* (2013.01); *H01M 10/0567* (2013.01); *H01M 10/0568* (2013.01); *H01M 2300/0025* (2013.01); *Y02E 60/13* (2013.01)

(58) Field of Classification Search
None
See application file for complete search history.

(56) References Cited

U.S. PATENT DOCUMENTS

2017/0204124 A1* 7/2017 Takahashi ........... H01M 10/052

FOREIGN PATENT DOCUMENTS

| CN | 106471000 | 3/2017 |
|---|---|---|
| EP | 3 165 528 | 5/2017 |

(Continued)

OTHER PUBLICATIONS

Nie et al., "Synthesis and characterization of a novel electrolyte based on bis[(perfluoroalkyl)sulfortyl]triimide trianion", Journal of Fluorine Chemistry, vol. 125, 2004, pp. 27-31.

(Continued)

*Primary Examiner* — Jonathan Crepeau
(74) *Attorney, Agent, or Firm* — Wenderoth, Lind & Ponack, L.L.P.

(57) ABSTRACT

Provided is a novel imidic acid compound having a divalent anion useful as a pharmaceutical intermediate, an agrochemical intermediate, an acid catalyst, a battery electrolyte or an antistatic agent. The imidic acid compound is a divalent imidic acid compound represented by the following general formula (1) or (2).

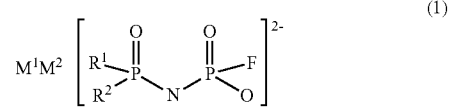

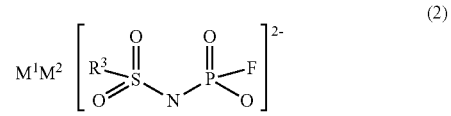

[In formulae (1) and (2), $R^1$ to $R^3$ represent a fluorine atom or an organic groups selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, and wherein a fluorine atom, an oxygen atom or an unsaturated bond may also be present in the organic group. $M^1$ and $M^2$ represent protons, metal cations or onium cations.]

12 Claims, No Drawings

(51) Int. Cl.
C09K 3/16 (2006.01)
H01M 10/0568 (2010.01)
C01B 25/455 (2006.01)
H01G 11/62 (2013.01)
H01M 10/052 (2010.01)
H01M 10/054 (2010.01)
H01M 6/16 (2006.01)

(56) References Cited

FOREIGN PATENT DOCUMENTS

| | | |
|---|---|---|
| JP | 2001-512714 | 8/2001 |
| WO | 2016/002774 | 1/2016 |

OTHER PUBLICATIONS

Geiculescu et al., "Dilithium bis[(perfluoroalkyl)sulfortyl]diimide salts as electrolytes for rechargeable lithium batteries", Journal of Fluorine Chemistry, vol. 125, 2004, pp. 1179-1185.
International Search Report dated Mar. 1, 2016 in International (PCT) Application No. PCT/JP2015/083795.

* cited by examiner

IMIDIC ACID COMPOUND HAVING DIVALENT ANION AND PROCESS FOR PRODUCING THE SAME

TECHNICAL FIELD

The present invention relates to an imidic acid compound having a divalent anion, which is useful as a pharmaceutical intermediate, an agrochemical intermediate, an acid catalyst, a battery electrolyte, and an antistatic agent, as well as a process for producing the same.

BACKGROUND ART

Conventionally broadly known sulfonylimidic acid compounds and phosphorylimidic acid compounds are useful substances as pharmaceutical intermediates and agrochemical intermediates, as well as acid catalysts, ionic liquids, and antistatic agents. These compounds have been used in recent years for electrolytes of energy devices, such as Li batteries, fuel cells, and electric double layer capacitors.

Electrolytes of these energy devices are required to have characteristics such as a high ionic conductivity. As a means for improving the ionic conductivity, for example, as disclosed in Patent Document 1, Non-patent Document 1, and Non-patent Document 2, there have been efforts to improve an ionic conductivity by increasing the number of counter cations within one molecule through the use of diimide, dimethide or triimide as anion. However, a perfluoroalkyl group is essential for these divalent or higher valent anions in order to increase acidity. However, the introduction of a perfluoroalkyl group is inefficient, since this results in an increase in the molecular weight of the anion, and a decrease in the number of counter cations per molecular weight. Furthermore, the molecular weight is high, so that the viscosity tends to increase to lower the ionic conductivity, when it is dissolved in the electrolytic solution of an energy device. Furthermore, a perfluoroalkyl group is very expensive and this is a disadvantage for industrial mass production. Furthermore, the use of a diimidic acid compound having a perfluoroalkylsulfonyl group or an imidic acid compound having a sulfonate group ($—SO_3^-$) is difficult, since these compounds corrode aluminum that is an electrode collector when used for electrolytes of energy devices.

PRIOR ART DOCUMENTS

Patent Document

Patent Document 1: JP Patent Publication (Kohyo) No. 2001-512714 A

Non-Patent Documents

Non-patent Document 1: Journal of Fluorine Chemistry, 125:27-31 (2004)
Non-patent Document 2: Journal of Fluorine Chemistry, 125:1179-1185 (2004)

SUMMARY OF THE INVENTION

Problem to be Solved by the Invention

As described above, an imidic acid compound or a methide acid compound having a divalent or higher valent anion disclosed in the prior art documents is not completely sufficient and remains to be improved. The present invention has been achieved in view of the above problems and provides a novel imidic acid compound having a divalent anion.

Means for Solving the Problems

The present inventors had made intensive studies to solve the above problems, and as a result, they have synthesized a novel divalent imidic acid compound having a fluorophosphate group ($—P(=O) FO^-$), and thus have completed the present invention.

Specifically, the present invention relates to a divalent imidic acid compound having a fluorophosphate group, which is represented by the following general formula (1) or (2).

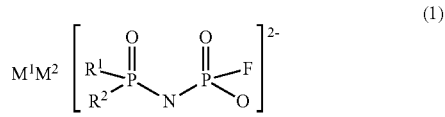

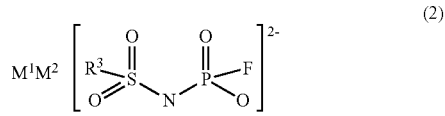

Wherein in formulae (1) and (2), $R^1$ to $R^3$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group; and wherein $M^1$ and $M^2$ each independently represent a proton, a metal cation or an onium cation.

The above $R^1$ to $R^3$ preferably represent a fluorine atom or an organic group selected from the group consisting of a C1-10 alkoxy group, a C2-10 alkenyloxy group and C2-10 alkynyloxy group.

The above alkoxy group is preferably selected from the group consisting of a methoxy group, an ethoxy group and a propoxy group. The above alkenyloxy group is preferably selected from the group consisting of a 1-propenyloxy group, a 2-propenyloxy group, a 2-butenyloxy group and a 3-butenyloxy group. The above alkynyloxy group is preferably selected from the group consisting of a 2-propynyloxy group and a 1,1-dimethyl-2-propynyloxy group.

Moreover, the above $R^1$ to $R^3$ are all preferably fluorine atoms.

Moreover, in the above general formula (1), $R^1$ preferably represents a fluorine atom, and, $R^2$ preferably represents an organic group selected from among a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group.

Furthermore, $M^1$ and $M^2$ as the counter cations of imide anions in the above general formulae (1) and (2) each preferably represent at least one cation selected from the group consisting of a proton, a lithium ion, a sodium ion, a potassium ion, a tetraalkylammonium ion and a tetraalkylphosphonium ion.

The present invention relates to an electrolyte for an electrochemical device comprising the above imidic acid compound.

Furthermore, the present invention relates to an antistatic agent comprising the above imidic acid compound.

Furthermore, the present invention relates to a process for producing an imidic acid compound represented by the following general formula (1)' (hereinafter, referred to as "1st production process"), which comprises, in the presence of an organic base or an inorganic base, reacting a fluorophosphoric amide salt ($M^1[PO_2F(NH_2)]$ and/or $M^2[PO_2F(NH_2)]$ wherein $M^1$ and $M^2$ represent protons, metal cations or onium cations) with a halogenated phosphate ($O=PR^1R^2X$ wherein X represents a halogen, and $R^1$ and $R^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group).

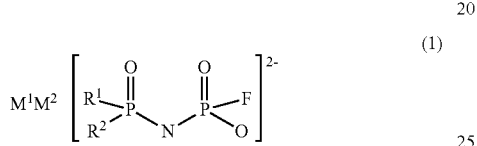

(1)

wherein in formula (1), $R^1$ and $R^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group; and $M^1$ and $M^2$ each independently represent a proton, a metal cation or an onium cation.

Furthermore, the present invention relates to a process for producing an imidic acid compound represented by the following general formula (1) (hereinafter, referred to as "$2^{nd}$ production process"), which comprises, in the presence of an organic base or an inorganic base, reacting phosphoric amide ($O=PR^1R^2(NH_2)$ wherein $R^1$ and $R^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group) with a fluorophosphate ($M^1[PO_2FX]$ and/or $M^2[PO_2FX]$ wherein X represents a halogen, and $M^1$ and $M^2$ represent protons, metal cations or onium cations).

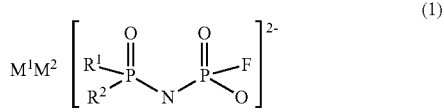

(1)

wherein in formula (1), $R^1$ and $R^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group; and wherein $M^1$ and $M^2$ each independently represent a proton, a metal cation or an onium cation.

Moreover, the present invention relates to a process for producing an imidic acid compound represented by the following general formula (2) (hereinafter, referred to as "$3^{rd}$ production process"), which comprises, in the presence of an organic base or an inorganic base, reacting a fluorophosphoric amide salt ($M^1[PO_2F(NH_2)]$ and/or $M^2[PO_2F(NH_2)]$ wherein $M^1$ and $M^2$ represent protons, metal cations or onium cations) with a sulfonyl halide ($R^3SO_2X$ wherein X represents a halogen, and $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and C6-10 aryloxy group, wherein a fluorine atom, an oxygen atom or an unsaturated bond may also be present in the organic group).

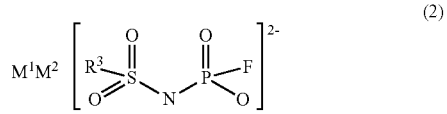

(2)

wherein in formula (2), $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group; and wherein $M^1$ and $M^2$ each independently represent a proton, a metal cation or an onium cation.

Furthermore, the present invention relates to a process for producing an imidic acid compound represented by the following general formula (2) (hereinafter, referred to as "$4^{th}$ production process"), which comprises, in the presence of an organic base or an inorganic base, reacting a sulfonyl amide ($R^3SO_2NH_2$ wherein $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and C6-10 aryloxy group, wherein a fluorine atom, an oxygen atom or an unsaturated bond may also be present in the organic group) with a fluorophosphate ($M^1[PO_2FX]$ and/or $M^2[PO_2FX]$ wherein X represents a halogen, and $M^1$ and $M^2$ represent protons, metal cations or onium cations).

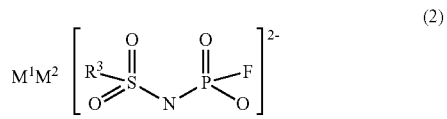

(2)

wherein in formula (2), $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group; and wherein $M^1$ and $M^2$ each independently represent a proton, a metal cation or an onium cation.

Effect of the Invention

According to the present invention, a novel divalent imidic acid compound having a fluorophosphate group (—P (=O)FO⁻) is provided. The divalent imidic acid compound is advantageous, for example, in that it has an ionic conductivity equivalent to or higher than that of the conventional divalent or higher valent imidic acid compounds and methide acid compounds having perfluoroalkyl groups, and may be produced inexpensively.

MODES FOR CARRYING OUT THE INVENTION

The present invention will be described below more specifically. However, the following constitutional features are merely examples of the embodiments of the present invention, and the present invention is not limited to these specific descriptions. Various modifications and variations can be made without departing from the scope of the present invention, and the present invention can be implemented.

Divalent Imidic Acid Compound

The present invention relates to a divalent imidic acid compound having a fluorophosphate group, which is represented by the following general formula (1) or (2).

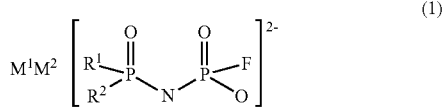

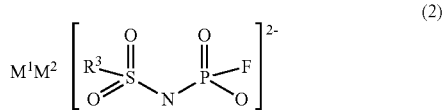

wherein in formulae (1) and (2), $R^1$ to $R^3$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group; and wherein M and $M^2$ each independently represent a proton, a metal cation or an onium cation.

Therefore, the imidic acid compound having a divalent anion according to the present invention is not the one in which a perfluoroalkyl group is introduced, and is neither a diimidic acid compound having a perfluoroalkylsulfonyl group nor an imidic acid compound having a sulfonate group (—SO₃⁻).

Examples of the counter cations ($M^1$ and $M^2$) of the above divalent imide anion include alkali metal cations such as a proton, a lithium ion, a sodium ion and a potassium ion; and alkaline-earth metal cations such as a magnesium ion and a calcium ion. Examples thereof further include onium cations represented by tetraalkylammonium ions such as a tetramethyl ammonium ion and a tetraethyl ammonium ion; and tetraalkylphosphonium ions such as a tetrabutylphosphonium ion. In addition, when a counter cation is a monovalent cation, 2 cations may exist in a mixed form. Moreover, for example, if $M^1$ is a divalent cation, $M^2$ is absent.

Cations, $M^1$ and $M^2$, of the above imidic acid compound are preferably protons, alkali metal cations or onium cations. Of these examples, $M^1$ and $M^2$ each more preferably represent at least one cation selected from the group consisting of a proton, a lithium ion, a sodium ion, a potassium ion, a tetraalkylammonium ion and a tetraalkylphosphonium ion in view of their solubility and ionic conductance in a nonaqueous solvent.

In the above formulae (1) and (2), examples of those represented by $R^1$ to $R^3$, specifically: examples of alkoxy groups include C1-10 alkoxy groups and fluorine-containing alkoxy groups such as a methoxy group, an ethoxy group, a propoxy group, an isopropoxy group, a butoxy group, a secondary butoxy group, a tertiary butoxy group, a pentyloxy group, a trifluoromethoxy group, a 2,2-difluoroethoxy group, a 2,2,2-trifluoroethoxy group, a 2,2,3,3-tetrafluoropropoxy group and a 1,1,1,3,3,3-hexafluoroisopropoxy group; examples of alkenyloxy groups include C2-10 alkenyloxy groups and fluorine-containing alkenyloxy groups such as a vinyloxy group, a 1-propenyloxy group, a 2-propenyloxy group, an isopropenyloxy group, a 2-butenyloxy group, a 3-butenyloxy group and a 1,3-butadienyloxy group; examples of alkynyloxy groups include C2-10 alkynyloxy groups and fluorine-containing alkynyloxy groups such as an ethynyloxy group, a 2-propynyloxy group and a 1,1-dimethyl-2-propynyloxy group; examples of cycloalkoxy groups include C3-10 cycloalkoxy groups and fluorine-containing cycloalkoxy groups such as a cyclopentyloxy group and a cyclohexyloxy group; examples of cycloalkenyloxy groups include C3-10 cycloalkenyloxy groups and fluorine-containing cycloalkenyloxy groups such as a cyclopentenyloxy group and a cyclohexenyloxy group; and examples of aryloxy groups include C6-10 aryloxy groups and fluorine-containing aryloxy groups such as a phenyloxy group, a tolyloxy group and a xylyloxy group.

$R^1$ to $R^3$ of the above imidic acid compound are preferably fluorine atoms, because its strong electron-withdrawing property of fluorine improves an ion dissociation degree and the lower anion size improves mobility, so as to significantly increase the degree of ionic conductance in a solution or a composition. Furthermore, the above $R^1$ to $R^3$ are preferably organic groups selected from the group consisting of an alkoxy group, an alkenyloxy group and an alkynyloxy group. Unlike the above alkoxy group, alkenyloxy group and alkynyloxy group, a hydrocarbon group with no intervening oxygen atom is not preferred because of its weak electron-withdrawing property that causes a decrease in an ion dissociation degree and a decrease in an ionic conductance in a solution or a composition. Furthermore, the higher number of carbons tends to result in an increased anion size and decreased ionic conductance in a solution or a composition. Hence, the number of carbons of the above organic group is preferably 6 or less. If the number of carbons is 6 or less, the resulting ionic conductance tends to be relatively high. The organic group is particularly preferably a group selected from the group consisting of a methoxy group, an ethoxy group, a propoxy group, a 1-propenyloxy group, a 2-propenyloxy group, a 2-butenyloxy group, a 3-butenyloxy group, a 2-propynyloxy group, and 1,1-dimethyl-2-propynyloxy group, because of their relatively small anion sizes.

More specific examples of the divalent imide anions described in the above general formulae (1) and (2) can include the following Compounds Nos. 1 to 11. However, the imide anions to be used in the present invention are not limited by the following examples.

Compound No. 1

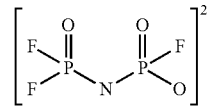

-continued

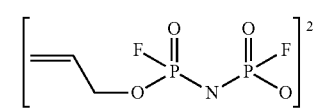

Compound No. 2

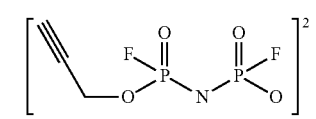

Compound No. 3

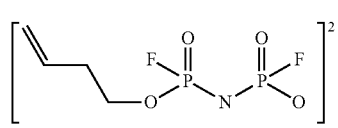

Compoound No. 4

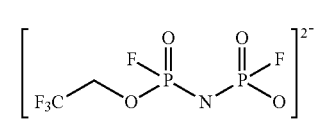

Compound No. 5

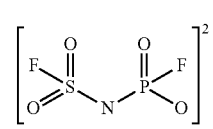

Compound No. 6

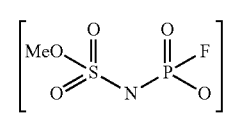

Compound No. 7

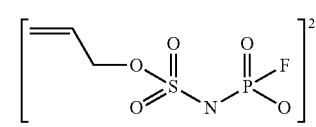

Compound No. 8

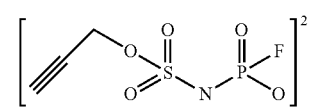

Comppound No. 9

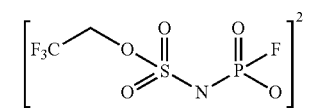

Compound No. 10

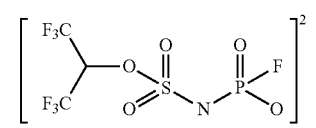

Compound No. 11

The divalent imidic acid compound having a fluorophosphate group according to the present invention can be used in any industrial field. For example, the divalent imidic acid compound is useful as an acid catalyst for organic synthesis, a raw material for a high polymer, an antistatic agent, and an electrolyte or an additive for electrolyte solution for energy devices. Moreover, the imidic acid compound of the present invention is a novel divalent imidic acid compound having a fluorophosphate anion, which has an effect of improving ion dissociation due to the strong electron-withdrawing property of fluorine, and contains a divalent cation within a single molecule. Hence, the imidic acid compound is expected to improve an ionic conductivity per molecule.

Process for Producing Divalent Imidic Acid Compound

The process for producing the divalent imidic acid compounds represented by the above general formulae (1) and (2) is not particularly limited.

For example, the compound represented by formula (1) can be synthesized (1$^{st}$ production process) by reacting a fluorophosphoric amide salt ($M^1[PO_2F(NH_2)]$ and/or $M^2[PO_2F(NH_2)]$ wherein $M^1$ and $M^2$ represent protons, metal cations or onium cations) with a halogenated phosphoric acid ($O=PR^1R^2X$ wherein X represents a halogen, and $R^1$ and $R^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group) in the presence of an organic base or an inorganic base.

Examples of the above fluorophosphoric amide salt include a fluorophosphoric amide (proton form), a lithium salt thereof, a sodium salt thereof, a potassium salt thereof, a cesium salt thereof, a magnesium salt thereof, a calcium salt thereof, an ammonium salt thereof, a triethylamine salt thereof, a tributylamine salt thereof, a N,N-diisopropyl ethylamine salt thereof, a pyridine salt thereof, a 4-dimethylamino pyridine salt thereof, a tetraethyl ammonium salt thereof, a methyltriethylammonium salt thereof, a tetraethylphosphonium salt thereof and a tetrabutylphosphonium salt thereof. Of these examples, a fluorophosphoric amide (proton form), a lithium salt thereof, a sodium salt thereof, a potassium salt thereof, an ammonium salt thereof, a triethylamine salt thereof, a tributylamine salt thereof, a N,N-diisopropyl ethylamine salt thereof, a pyridine salt thereof, and a 4-dimethylamino pyridine salt thereof are preferred in view of its solubility to a reaction solvent.

Examples of the above halogenated phosphic acid include phosphoryl chloride difluoride, phosphoryl bromide difluoride, methyl difluorophosphate, methyl fluorochlorophosphate, methyl fluorobromophosphate, dimethyl fluorophosphate, dimethyl chlorophosphate, dimethyl bromophosphate, ethyl difluorophosphate, ethyl fluorochlorophosphate, ethyl fluorobromophosphate, diethyl fluorophosphate, diethyl chlorophosphate, diethyl bromophosphate, (n-propyl)difluorophosphate, (n-propyl) fluorochlorophosphate, (n-propyl) fluorobromophosphate, di(n-propyl)fluorophosphate, di(n-propyl)chlorophosphate, di(n-propyl)bromophosphate, isopropyl difluorophosphate, isopropyl fluorochlorophosphate, isopropyl fluorobromophosphate, diisopropyl fluorophosphate, diisopropyl chlorophosphate, diisopropyl bromophosphate, (1-propenyl) difluorophosphate, (1-propenyl) fluorochlorophosphate, (1-propenyl) fluorobromophosphate, di(1-propenyl)fluorophosphate, di(1-propenyl)chlorophosphate, di(1-propenyl) bromophosphate, (2-propenyl)difluorophosphate, (2-propenyl) fluorochlorophosphate, (2-propenyl) fluorobromophosphate, di(2-propenyl)fluorophosphate, di(2-propenyl)chlorophosphate, di(2-propenyl)bromophosphate, (2-butenyl)difluorophosphate, (2-butenyl)fluorochlorophosphate, (2-butenyl)fluorobromophosphate, di(2-butenyl)fluorophosphate, di(2-butenyl)chlorophosphate, di(2-butenyl)bromophosphate, (3-butenyl)difluorophosphate, (3-butenyl)fluorochlorophosphate, (3-butenyl)fluorobromophosphate, di(3-butenyl)fluorophosphate, di(3-butenyl) chlorophosphate, di(3-butenyl)bromophosphate, (2-propynyl) difluorophosphate, (2-propynyl)fluorochlorophosphate, (2-propynyl)fluorobromophosphate, di(2-propynyl)fluorophosphate, di(2-propynyl)chlorophosphate, di(2-propynyl) bromophosphate, (1,1-dimethyl-2-propynyl)difluorophosphate, (1,1-dimethyl-2-propynyl)fluorochlorophosphate, (1,1-dimethyl-2-propynyl)fluorobromophosphate, di(1,1-dimethyl-2-propynyl)fluorophosphate, di(1,1-dimethyl-2-propynyl)chlorophosphate, di(1,1-dimethyl-2-propynyl)bromophosphate, (2,2-difluoroethyl)difluorophosphate, (2,2-difluoroethyl)fluorochlorophosphate, (2,2-difluoroethyl)fluorobromophosphate, di(2,2-difluoroethyl)fluorophosphate, di(2,2-difluoroethyl)chlorophosphate, di(2,2-difluoroethyl)bromophosphate, (2,2,2-trifluoroethyl)difluorophosphate, (2,2,2-trifluoroethyl)fluorochlorophosphate, (2,2,2-trifluoroethyl)fluorobromophosphate, di(2,2,2-trifluoroethyl)fluorophosphate, di(2,2,2-trifluoroethyl)chlorophosphate, di(2,2,2-trifluoroethyl)bromophosphate, (1,1,1,3,3,3-hexafluoroisopropyl)difluorophosphate, (1,1,1,3,3,3-hexafluoroisopropyl)fluorochlorophosphate, (1,1,1,3,3,3-hexafluoroisopropyl)fluorobromophosphate, di(1,1,1,3,3,3-hexafluoroisopropyl)fluorophosphate, di(1,1,1,3,3,3-hexafluoroisopropyl)chlorophosphate, di(1,1,1,3,3,3-hexafluoroisopropyl)bromophosphate, (2,2,3,3-tetrafluoropropyl)difluorophosphate, (2,2,3,3-tetrafluoropropyl)fluorochlorophosphate, (2,2,3,3-tetrafluoropropyl)fluorobromophosphate, di(2,2,3,3-tetrafluoropropyl)fluorophosphate, di(2,2,3,3-tetrafluoropropyl)chlorophosphate, di(2,2,3,3-tetrafluoropropyl)bromophosphate, cyclopentyl difluorophosphate, cyclopentyl fluorochlorophosphate, cyclopentyl fluorobromophosphate, dicyclopentyl fluorophosphate, dicyclopentyl chlorophosphate, dicyclopentyl bromophosphate, cyclohexyl difluorophosphate, cyclohexyl fluorochlorophosphate, cyclohexyl fluorobromophosphate, dicyclohexyl fluorophosphate, dicyclohexyl chlorophosphate, dicyclohexyl bromophosphate, cyclopentenyl difluorophosphate, cyclopentenyl fluorochlorophosphate, cyclopentenyl fluorobromophosphate, dicyclopentenyl fluorophosphate, dicyclopentenyl chlorophosphate, dicyclopentenyl bromophosphate, cyclohexenyl difluorophosphate, cyclohexenyl fluorochlorophosphate, cyclohexenyl fluorobromophosphate, dicyclohexenyl fluorophosphate, dicyclohexenyl chlorophosphate, dicyclohexenyl bromophosphate, phenyl difluorophosphate, phenyl fluorochlorophosphate, phenyl fluorobromophosphate, diphenyl fluorophosphate, diphenyl chlorophosphate, diphenyl bromophosphate, tolyl difluorophosphate, tolyl fluorochlorophosphate, tolyl fluorobromophosphate, ditolyl fluorophosphate, ditolyl chlorophosphate, ditolyl bromophosphate, xylyl difluorophosphate, xylyl fluorochlorophosphate, xylyl fluorobromophosphate, dixylyl fluorophosphate, dixylyl chlorophosphate, and dixylyl bromophosphate. Of these examples, phosphoryl chloride difluoride, methyl difluorophosphate, methyl fluorochlorophosphate, ethyl difluorophosphate, ethyl fluorochlorophosphate, (n-propyl)difluorophosphate, (n-propyl) fluorochlorophosphate, isopropyl difluorophosphate, isopropyl fluorochlorophosphate, (1-propenyl)difluorophosphate, (1-propenyl) fluorochlorophosphate, (2-propenyl)difluorophosphate, (2-propenyl) fluorochlorophosphate, (2-butenyl)difluorophosphate, (2-butenyl) fluorochlorophosphate, (3-butenyl)difluorophosphate, (3-butenyl)fluorochlorophosphate, (2-propynyl)difluorophosphate, (2-propynyl)fluorochlorophosphate, (1,1-dimethyl-2-propynyl)difluorophosphate, (1,1-dimethyl-2-propynyl)fluorochlorophosphate, (2,2-difluoroethyl) difluorophosphate, (2,2-difluoroethyl) fluorochlorophosphate, (2,2,2-trifluoroethyl) difluorophosphate, (2,2,2-trifluoroethyl) fluorochlorophosphate, (1,1,1,3,3,3-hexafluoroisopropyl) difluorophosphate, (1,1,1,3,3,3-hexafluoroisopropyl) fluorochlorophosphate, (2,2,3,3-tetrafluoropropyl) difluorophosphate and (2,2,3,3-tetrafluoropropyl)fluorochlorophosphate are preferred in view of the ionic conductance of the thus generated divalent imide compound.

Furthermore, the compound represented by formula (1) can be synthesized ($2^{nd}$ production process) by reacting a phosphoric amide (O=PR$^1$R$^2$ (NH$_2$) wherein R$^1$ and R$^2$ each independently represent a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group) with a fluorophosphate (M$^1$[PO$_2$FX] and/or M$^2$[PO$_2$FX] wherein X represents a halogen, and M$^1$ and M$^2$ represent protons, metal cations or onium cations) in the presence of an organic base or an inorganic base.

Examples of the above phosphoric amide include difluorophosphoric amide, methyl amidofluorophosphate, dimethyl amidophosphate, ethyl amidofluorophosphate, diethyl amidophosphate, (n-propyl)amidofluorophosphate, di(n-propyl)amidophosphate, isopropyl amidofluorophosphate, diisopropyl amidophosphate, (1-propenyl)amidofluorophosphate, di(1-propenyl)amidophosphate, (2-propenyl)amidofluorophosphate, di(2-propenyl)amidophosphate, (2-butenyl)amidofluorophosphate, di(2-butenyl)amidophosphate, (3-butenyl)amidofluorophosphate, di(3-butenyl)amidophosphate, (2-propynyl)amidofluorophosphate, di(2-propynyl) amidophosphate, (1,1-dimethyl-2-propynyl)amidofluorophosphate, di(1,1-dimethyl-2-propynyl)amidophosphate, (2,2-difluoroethyl)amidofluorophosphate, di(2,2-difluoroethyl)amidophosphate, (2,2,2-trifluoroethyl)amidofluorophosphate, di(2,2,2-trifluoroethyl)amidophosphate, (1,1,1,3,3,3-hexafluoroisopropyl)amidofluorophosphate, di(1,1,1,3,3,3-hexafluoroisopropyl)amidophosphate, (2,2,3,3-tetrafluoropropyl)amidofluorophosphate, di(2,2,3,3-tetrafluoropropyl)amidophosphate, cyclopentyl amidofluorophosphate, dicyclopentyl amidophosphate, cyclohexyl amidofluorophosphate, dicyclohexyl amidophosphate, cyclopentenyl amidofluorophosphate, dicyclopentenyl amidophosphate, cyclohexenyl amidofluorophosphate, dicyclohexenyl amidophosphate, phenyl amidofluorophosphate, diphenyl amidophosphate, tolyl amidofluorophosphate, ditolyl amidophosphate, xylyl amidofluorophosphate and dixylyl amidophosphate. Of these examples, difluorophosphoric amide, methyl amidofluorophosphate, ethyl amidofluorophosphate, (n-propyl) amidofluorophosphate, isopropyl amidofluorophosphate, (1-propenyl)amidofluorophosphate, (2-propenyl)amidofluorophosphate, (2-butenyl) amidofluorophosphate, (3-butenyl) amidofluorophosphate, (2-propynyl)amidofluorophosphate, (1,1-dimethyl-2-propynyl)amidofluorophosphate, (2,2-difluoroethyl)amidofluorophosphate, (2,2,2-trifluoroethyl) amidofluorophosphate, (1,1,1,3,3,3-hexafluoroisopropyl) amidofluorophosphate, and (2,2,3,3-tetrafluoropropyl) amidofluorophosphate are preferred in view of the ionic conductance of the thus generated divalent imide compound.

Examples of the above fluorophosphate include difluorophosphoric acid (proton form), lithium difluorophosphate, sodium difluorophosphate, potassium difluorophosphate, cesium difluorophosphate, magnesium difluorophosphate, calcium difluorophosphate, ammonium difluorophosphate, triethylamine difluorophosphate, tributylamine difluorophosphate, (N,N-diisopropyl ethyl amine) difluorophosphate, pyridine difluorophosphate, (4-dimethylaminopyridine) difluorophosphate, tetraethylammonium difluorophosphate, methyl triethyl ammonium difluorophosphate, tetraethyl phosphonium difluorophosphate, tetraethyl phosphonium difluorophosphate, fluorochlorophosphoric acid (proton form), lithium fluorochlorophosphate, sodium fluorochlorophosphate, potassium fluorochlorophosphate, cesium fluorochlorophosphate, magnesium fluorochlorophosphate, calcium fluorochlorophosphate, ammonium fluorochlorophosphate, triethylamine fluorochlorophosphate, tributylamine fluorochlorophosphate, (N,N-diisopropylethylamine)fluorochlorophosphate, pyridine fluorochlorophosphate, (4-dimethylaminopyridine) fluorochlorophosphate, tetraethyl ammonium fluorochlorophosphate, methyltriethyl ammonium fluorochlorophosphate, tetraethyl phosphonium fluorochlorophosphate and tetrabutyl phosphonium fluorochlorophosphate. Of these examples, difluorophosphoric acid (proton form), lithium difluorophosphate, sodium difluorophosphate, potassium difluorophosphate, ammonium difluorophosphate, triethylamine difluorophosphate, tributylamine difluorophosphate, (N,N-diisopropylethylamine)difluorophosphate, pyridine difluorophosphate, (4-dimethylaminopyridine)difluorophosphate, fluorochlorophosphoric acid (proton form), lithium fluorochlorophosphate, sodium fluorochlorophosphate, potassium fluorochlorophosphate, ammonium fluorochlorophosphate, triethylamine fluorochlorophosphate, tributylamine fluorochlorophosphate, (N,N-diisopropylethylamine)fluorochlorophosphate, pyridine fluorochlorophosphate, (4-dimethylaminopyridine) fluorochlorophosphate are preferred in view of its solubility to a reaction solvent.

Furthermore, for example, the compound represented by formula (2) can be synthesized (3rd production process) by reacting a fluorophosphoramide salt ($M^1[PO_2F(NH_2)]$ and/or $M^2[PO_2F(NH_2)]$ wherein $M^1$ and $M^2$ represent protons, metal cations or onium cations) with a sulfonyl halide ($R^3SO_2X$ wherein X represents a halogen, and $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom, or an unsaturated bond may also be present in the organic group) in the presence of an organic base or an inorganic base.

Examples of the above fluorophosphoric amide salt include salts similar to those in the case of the $1^{st}$ production process. Particularly in view of its solubility to a reaction solvent, fluorophosphoric amide (proton form), a lithium salt thereof, a sodium salt thereof, a potassium salt thereof, an ammonium salt thereof, a triethylamine salt thereof, a tributylamine salt thereof, a N,N-diisopropylethyl amine salt thereof, a pyridine salt thereof and a 4-dimethylamino pyridine salt thereof are preferred.

Examples of the above sulfonyl halide include sulfuryl fluoride, sulfuryl chloride fluoride, sulfuryl bromide fluoride, sulfuryl iodide fluoride, sulfuryl fluoride methyl ester, sulfuryl chloride methyl ester ($MeOSO_2Cl$), sulfuryl bromide methyl ester, sulfuryl iodide methyl ester, sulfuryl fluoride ethyl ester, sulfuryl chloride ethyl ester, sulfuryl bromide ethyl ester, sulfuryl iodide ethyl ester, sulfuryl fluoride (n-propyl)ester, sulfuryl chloride (n-propyl)ester, sulfuryl bromide (n-propyl)ester, sulfuryl iodide(n-propyl)ester, sulfuryl fluoride isopropyl ester, sulfuryl chloride isopropyl ester, sulfuryl bromide isopropyl ester, sulfuryl iodide isopropyl ester, sulfuryl fluoride (1-propenyl)ester, sulfuryl chloride (1-propenyl)ester, sulfuryl bromide (1-propenyl)ester, sulfuryl iodide(1-propenyl)ester, sulfuryl fluoride(2-propenyl)ester, sulfuryl chloride(2-propenyl)ester, sulfuryl bromide (2-propenyl)ester, sulfuryl iodide (2-propenyl)ester, sulfuryl fluoride (2-butenyl)ester, sulfuryl chloride (2-butenyl)ester, sulfuryl bromide (2-butenyl)ester, sulfuryl iodide (2-butenyl)ester, sulfuryl fluoride (3-butenyl) ester, sulfuryl chloride (3-butenyl)ester, sulfuryl bromide (3-butenyl)ester, sulfuryl iodide (3-butenyl)ester, sulfuryl fluoride (2-propynyl)ester, sulfuryl chloride (2-propynyl) ester, sulfuryl bromide (2-propynyl)ester, sulfuryl iodide (2-propynyl)ester, sulfuryl fluoride (1,1-dimethyl-2-propynyl)ester, sulfuryl chloride (1,1-dimethyl-2-propynyl)ester, sulfuryl bromide (1,1-dimethyl-2-propynyl)ester, sulfuryl iodide (1,1-dimethyl-2-propynyl)ester, sulfuryl fluoride (2,2-difluoroethyl)ester, sulfuryl chloride (2,2-difluoroethyl) ester, sulfuryl bromide (2,2-difluoroethyl)ester, sulfuryl iodide (2,2-difluoroethyl)ester, sulfuryl fluoride (2,2,2-trifluoroethyl)ester, sulfuryl chloride (2,2,2-trifluoroethyl)ester, sulfuryl bromide (2,2,2-trifluoroethyl)ester, sulfuryl iodide (2,2,2-trifluoroethyl)ester, sulfuryl fluoride (1,1,1,3,3,3-hexafluoroisopropyl)ester, sulfuryl chloride (1,1,1,3,3,3-hexafluoroisopropyl)ester, sulfuryl bromide (1,1,1,3,3,3-hexafluoroisopropyl)ester, sulfuryl iodide (1,1,1,3,3,3-hexafluoroisopropyl)ester, sulfuryl fluoride (2,2,3,3-tetrafluoropropyl)ester, sulfuryl chloride (2,2,3,3-tetrafluoropropyl)ester, sulfuryl bromide (2,2,3,3-tetrafluoropropyl)ester, sulfuryl iodide (2,2,3,3-tetrafluoropropyl)ester, sulfuryl fluoride cyclopentyl ester, sulfuryl chloride cyclopentyl ester, sulfuryl bromide cyclopentyl ester, sulfuryl iodide cyclopentyl ester, sulfuryl fluoride cyclohexyl ester, sulfuryl chloride cyclohexyl ester, sulfuryl bromide cyclohexyl ester, sulfuryl iodide cyclohexyl ester, sulfuryl fluoride cyclopentenyl ester, sulfuryl chloride cyclopentenyl ester, sulfuryl bromide cyclopentenyl ester, sulfuryl iodide cyclopentenyl ester, sulfuryl fluoride cyclohexenyl ester, sulfuryl chloride cyclohexenyl ester, sulfuryl bromide cyclohexenyl ester, sulfuryl iodide cyclohexenyl ester, sulfuryl fluoride phenyl ester, sulfuryl chloride phenyl ester, sulfuryl bromide phenyl ester, sulfuryl iodide phenyl ester, sulfuryl fluoride tolyl ester, sulfuryl chloride tolyl ester, sulfuryl bromide tolyl ester, sulfuryl iodide tolyl ester, sulfuryl fluoride xylyl ester, sulfuryl chloride xylyl ester, sulfuryl bromide xylyl ester, and sulfuryl iodide xylyl ester. Of these examples, sulfuryl fluoride, sulfuryl chloride fluoride, sulfuryl fluoride methyl ester, sulfuryl chloride methyl ester, sulfuryl fluoride ethyl ester, sulfuryl chloride ethyl ester, sulfuryl fluoride (n-propyl) ester, sulfuryl chloride (n-propyl)ester, sulfuryl fluoride isopropyl ester, sulfuryl chloride isopropyl ester, sulfuryl fluoride (1-propenyl)ester, sulfuryl chloride (1-propenyl)ester, sulfuryl fluoride (2-propenyl)ester, sulfuryl chloride (2-propenyl)ester, sulfuryl fluoride (2-butenyl)ester, sulfuryl chloride (2-butenyl)ester, sulfuryl fluoride (3-butenyl)ester, sulfuryl chloride (3-butenyl)ester, sulfuryl fluoride (2-propynyl)ester, sulfuryl chloride (2-propynyl)ester, sulfuryl fluoride (1,1-dimethyl-2-propynyl)ester, sulfuryl chloride (1,1-dimethyl-2-propynyl)ester, sulfuryl fluoride (2,2-difluoroethyl)ester, sulfuryl chloride (2,2-difluoroethyl) ester, sulfuryl fluoride (2,2,2-trifluoroethyl)ester, sulfuryl chloride (2,2,2-trifluoroethyl)ester, sulfuryl fluoride (1,1,1,3,3,3-hexafluoroisopropyl)ester, sulfuryl chloride (1,1,1,3,3,3-hexafluoroisopropyl)ester, sulfuryl fluoride (2,2,3,3-tetrafluoropropyl)ester and sulfuryl chloride (2,2,3,3-tetrafluoropropyl)ester are preferred in view of the ease for removal of unreacted residual sulfonyl halides and the ionic conductance of the thus generated divalent imide compound.

Furthermore, the compound represented by formula (2) can be synthesized ($4^{th}$ production process) by reacting a sulfonyl amide ($R^3SO_2NH_2$ wherein $R^3$ represents a fluorine atom or an organic group selected from a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group) with a fluorophosphate ($M^1[PO_2FX]$ and/or $M^2[PO_2FX]$ wherein X represents a halogen, and $M^1$ and $M^2$ represent protons, metal cations or onium cations) in the presence of an organic base or an inorganic base.

Examples of the above sulfonyl amide include fluorosulfonyl amide, methyl sulfamate, ethyl sulfamate, (n-propyl) sulfamate, isopropyl sulfamate, (1-propenyl)sulfamate, (2-propenyl)sulfamate, (2-butenyl)sulfamate, (3-butenyl) sulfamate, (2-propynyl)sulfamate, (1,1-dimethyl-2-propynyl)sulfamate, (2,2-difluoroethyl)sulfamate, (2,2,2-trifluoroethyl)sulfamate, (1,1,1,3,3,3-hexafluoroisopropyl) sulfamate, (2,2,3,3-tetrafluoropropyl)sulfamate, cyclopentyl sulfamate, cyclohexyl sulfamate, cyclopentenyl sulfamate, cyclohexenyl sulfamate, phenyl sulfamate, tolyl sulfamate and xylyl sulfamate. Of these examples, fluorosulfonyl amide, methyl sulfamate, ethyl sulfamate, (n-propyl)sulfamate, isopropyl sulfamate, (1-propenyl)sulfamate, (2-propenyl)sulfamate, (2-butenyl)sulfamate, (3-butenyl)sulfamate, (2-propynyl)sulfamate, (1,1-dimethyl-2-propynyl)sulfamate, (2,2-difluoroethyl)sulfamate, (2,2,2-trifluoroethyl) sulfamate, (1,1,1,3,3,3-hexafluoroisopropyl)sulfamate and (2,2,3,3-tetrafluoropropyl)sulfamate are preferred in view of particularly the ionic conductance of the thus generated divalent imide compound.

Examples of the above fluorophosphate include those similar to the case of the $2^{nd}$ production process. Of these examples, difluorophosphoric acid (proton form), lithium difluorophosphate, sodium difluorophosphate, potassium difluorophosphate, ammonium difluorophosphate, triethylamine difluorophosphate, tributylamine difluorophosphate, (N,N-diisopropylethylamine)difluorophosphate, pyridine difluorophosphate, (4-dimethylaminopyridine) difluorophosphate, fluorochlorophosphoric acid (proton form), lithium fluorochlorophosphate, sodium fluorochlorophosphate, potassium fluorochlorophosphate, ammonium fluorochlorophosphate, triethylamine fluorochlorophosphate, tributylamine fluorochlorophosphate, (N,N-diisopropylethylamine)fluorochlorophosphate, pyridine fluorochlorophosphate, and (4-dimethylaminopyridine)fluorochlorophosphate are preferred in view of particularly its solubility to a reaction solvent.

Examples of the bases to be used in the above $1^{st}$ to $4^{th}$ production processes include organic bases including: tertiary amines such as trimethylamine, triethylamine, N-ethyl diisopropylamine, tri-n-propylamine, triisopropylamine, tri-n-butylamine, trioctylamine, tridecylamine, triphenylamine, tribenzylamine, tris (2-ethylhexyl)amine, N,N-dimethyl decylamine, N-benzyl dimethylamine, N-butyl dimethylamine, N,N-dimethyl cyclohexylamine, N,N,N',N'-tetramethyl ethylene diamine, N,N-dimethyl aniline, N,N-diethyl aniline, 1,4-diazabicyclo[2.2.2]octane, N-methyl pyrrolidine, N-methyl piperidine, N-methyl morpholine, N-ethyl morpholine, N,N'-dimethyl piperazine, N-methyl pipecoline, N-methylpyrrolidone, N-vinyl-pyrrolidone, bis(2-dimethylamino-ethyl)ether, N,N,N,N',N''-pentamethyl-diethylenetriamine, triethanolamine, tripropanolamine, dimethylethanolamine, dimethylaminoethoxyethanol, N,N-dimethylamino propyl amine, N,N,N',N',N''-pentamethyldipropylenetriamine, tris(3-dimethylaminopropyl)amine, tetramethyl imino-bis (propylamine) and N,N-diethyl-ethanolamine; nitrogen-containing aromatic heterocyclic compounds such as pyridine, 2,4,6-trimethyl pyridine, 3,5,6-trimethyl pyridine, 4-dimethylamino pyridine, 2,3-lutidine, 2,4-lutidine, 2,6-lutidine, 3,4-lutidine, 3,5-lutidine, pyrimidine, pyridazine, pyrazine, oxazole, isoxazole, thiazole, isothiazole, imidazole, 1,2-dimethyl imidazole, 3-(dimethylamino)propyl imidazole, pyrazole, furazan, quinolone, isoquinoline, purine, 1H-indazole, quinazoline, cinnoline, quinoxaline, phthalazine, pteridine, phenanthridine, 2,6-di-t-butylpyridine, 2,2'-bipyridine, 4,4'-dimethyl-2,2'-bipyridyl, 5,5'-dimethyl-2,2'-bipyridyl, 6,6'-di-t-butyl-2,2'-dipyridyl, 4,4'-diphenyl-2,2'-bipyridyl, 1,10-phenanthroline, 4,7-dimethyl-1,10-phenanthroline, 5,6-dimethyl-1,10-phenanthroline and 4,7-diphenyl-1,10-phenanthroline; imine compounds such as 1,8-diazabicyclo[5.4.0]undeca-7-ene and 1,5-diazabicyclo [4.3.0]non-5-ene; alkyl lithium such as n-butyl lithium, sec-butyl lithium and tert-butyl lithium; and Grignard reagents such as methyl magnesium chloride and methyl magnesium bromide, or inorganic bases including lithium hydride, sodium hydride, potassium hydride, calcium hydride, sodium carbonate and potassium carbonate. Of these examples, trimethylamine, triethylamine, N-ethyl diisopropyl amine, tripropyl amine, tri-n-butylamine, 4-dimethylamino pyridine, 2,3-lutidine, 2,4-lutidine, 2,6-lutidine, 3,4-lutidine, 3,5-lutidine, 2,4,6-trimethyl pyridine, 3,5, 6-trimethyl pyridine, n-butyllithium, lithium hydride, sodium hydride, and potassium hydride are preferred in view of particularly the ease of handling and the ease for removal of bases remaining after reaction.

Any reaction in the above $1^{st}$ to $4^{th}$ production processes are desirably performed in a nonaqueous solvent. Any nonaqueous solvent can be used herein as long as the imidic acid compound of the present invention can be obtained. Examples thereof include halocarbon such as dichloromethane, ethers such as diethyl ether and tetrahydrofuran, nitriles such as acetonitrile, esters such as ethyl acetate, carbonates such as dimethyl carbonate, N,N-dimethyl formamide and dimethyl sulfoxide. When the above organic bases are liquids, these organic bases can be caused to function as solvents. In addition, the reaction solvents may be used singly or in a combination of two or more solvents used at any ratio.

Furthermore, any reaction temperature can be employed for the above $1^{st}$ to $4^{th}$ production processes, as long as the imidic acid compound of the present invention can be obtained. The reaction temperature is generally, −30° C. or higher, preferably −10° C. or higher, and is generally 150° C. or lower and preferably 100° C. or lower. The use of the temperature lower than the lower limit of this range tends to result in a lower reaction rate and longer reaction time. Moreover, the use of the temperature higher than the upper limit thereof may cause the decomposition or the like of reaction raw materials or products. In particular, when halogenated phosphate is added, the temperature is desirably kept at 30° C. or lower.

Furthermore, any pressure can be applied for reaction in the above $1^{st}$ to $4^{th}$ production processes, as long as the imidic acid compound of the present invention can be obtained. A reaction can be performed under atmospheric conditions (0.1 MPa (absolute pressure)), or under reduced conditions or pressurized conditions using a pressure-resistant reactor.

Furthermore, while any reaction time for the above $1^{st}$ to $4^{th}$ production processes may be arbitrarily employed, as long as the imidic acid compound of the present invention can be obtained. It is sufficient that a reaction is generally performed for 0.5 to 48 hours and the reaction time may differ depending on the substrates and reaction conditions to be used. Accordingly, it is preferable that the progress of the reaction is traced by analytical means such as gas chromatography, liquid chromatography and NMR, and then that the time point at which most of the raw materials have disappeared in the course of the trace of the reaction is designated as the end point.

Moreover, in the above $1^{st}$ and $2^{nd}$ production processes, any ratio of a halogenated phosphate to a fluorophosphoramide salt as raw materials, or, any ratio of a phosphoric amide to a fluorophosphate as raw materials may be employed, as long as the imidic acid compound of the present invention can be obtained. When the ratio is represented by "(halogenated phosphate in molar amount)/(fluorophosphoric amide salt in molar amount)" or "(phosphoramide in molar amount)/(fluorophosphate in molar amount)," it is desirably generally 0.8 or more, preferably 1.0 or more, or generally 3.0 or less, preferably 2.0 or less. The use of the ratio lower than the lower limit of this range tends to result in a lower yield since the raw material, fluorophosphoramide salt or fluorophosphate remains unreacted. The use of the ratio higher than the upper limit results in a waste of the raw material for reaction, and undesirable reactions other than the targeted reaction can take place.

Moreover, the reaction is preferably performed with the amount of bases (organic bases or inorganic bases), which is generally 1.5 moles or more, and preferably 2.0 moles or more, relative to 1 mole of the fluorophosphoric amide salt or the fluorophosphate. The amount lower the lower limit of this range tends to result in a lower yield since the raw materials for reaction remain unreacted.

Furthermore, in the above $3^{rd}$ and $4^{th}$ production processes, the ratio of a sulfonyl halide to a fluorophosphoric amide salt as raw materials, or the ratio of a sulfonyl amide to a fluorophosphate as raw materials may be any ratio, as long as the imidic acid compound of the present invention can be obtained. When the ratio is represented by "(sulfonyl halide in molar amount)/(fluorophosphoramide salt in molar amount)" or "(sulfonyl amide in molar amount)/(fluorophosphate in molar amount)", it is desirable that the ratio is generally 0.8 or more, preferably 1.0 or more, and is generally 3.0 or less, and preferably 2.0 or less. The use of the ratio lower than the lower limit of this range tends to result in a lower yield since the raw material, the fluorophosphoramide salt or the fluorophosphate remains unreacted. The use of the ratio higher than the upper limit results in a waste of the raw material for reaction, and undesirable reactions other than the targeted reaction can take place.

Moreover, the reaction is preferably performed with the amount of bases (organic bases or inorganic bases), which is generally 1.5 moles or more, and preferably 2.0 moles or more relative to 1 mole of a fluorophosphoric amide salt or a fluorophosphate. The use of the amount lower than the lower limit of this range tends to result in a lower yield since the raw material for reaction remains unreacted.

Furthermore, in the above $1^{st}$ to $4^{th}$ production processes, a procedure for exchanging the cations of the thus obtained imidic acid compound with another type of cations may be performed. Any method for the cation exchange may be employed without any particular limitation. For example, ion exchange with the use of a metal salt or an onium salt in a nonaqueous solvent solution or a 2-phase system of the nonaqueous solvent solution with an aqueous solution, and an ion exchange resin can be used. Furthermore, the cation exchange may be performed at plural times. For example, the cations are exchanged with protons using an acid ion exchange resin, and then the protons can be exchanged with target cations using a metal salt or an onium salt. Furthermore, a metal salt or an onium salt is added in advance into the reaction system in the $1^{st}$ to $4^{th}$ production processes, and then the cation exchange can be performed during the reaction. In this case, a metal salt or an onium salt to be added is not particularly limited and may be any salt that does not adversely affect the reaction. Examples thereof include a metal halide, a tetraalkyl ammonium halide and a tetraalkyl phosphonium halide. Furthermore, the cation exchange may be performed with the above bases (organic bases or inorganic bases).

Moreover, in general, the thus obtained product is purified, so that the imidic acid compound of the present invention is obtained. In this case, any purification method can be employed without any particular limitation. For example, purification by recrystallization, purification by reprecipitation, or the like can be employed. In addition, the above purification procedure may be performed before, and/or after the above cation exchange.

EXAMPLES

The present invention will be more specifically described with reference to the following Examples. However, the scope of the present invention is not limited by these Examples.

Example 1-1 Synthesis of Dilithium Salt of Compound No. 1 ($1^{st}$ Production Process)

Triethylamine (2.0 g, 20 mmol) was slowly added dropwise to a flask containing fluorophosphoramide triethylamine salt($Et_2NH[PO_2F(NH_2)]$) (2.0 g, 9.9 mmol), phosphorus oxydifluorochloride ($POF_2Cl$) (1.8 g, 15 mmol) and acetonitrile (60 g) under an ice-cooling condition, followed by 2 hours of agitation at room temperature after completion of the addition. The thus obtained reaction product was subjected to cation exchange, thereby obtaining a crude dilithium salt. The resultant was purified by reprecipitation using an acetonitrile solvent, so that compound No. 1 dilithium salt (1.1 g, 5.9 mmol) was obtained.

Example 1-2 Synthesis of Dilithium Salt of Compound No. 1 ($2^{nd}$ Production Process)

Triethylamine (2.6 g, 26 mmol) was slowly added dropwise to a flask containing difluorophosphoramide ($H_2NPOF_2$) (1.5 g, 15 mmol), lithium chlorofluorophosphate ($LiPO_2FCl$) (1.5 g, 12 mmol), lithium chloride (0.59 g, 14 mmol) and tetrahydrofuran (50 g) under an ice-cooling condition, followed by 28 hours of agitation at 50° C. after completion of the addition. The thus obtained reaction product was purified by reprecipitation using an acetonitrile solvent, to yield dilithium salt of Compound No. 1 (0.82 g, 4.2 mmol).

Example 1-3 Synthesis of di(tetraethyl ammonium) salt of Compound No. 1 ($1^{st}$ production process)

Triethylamine (2.2 g, 22 mmol) was slowly added dropwise to a flask containing fluorophosphoramide.potassium salt ($K[PO_2F(NH_2)]$) (1.4 g, 10 mmol), phosphorus oxydifluorochloride ($POF_2Cl$) (1.8 g, 15 mmol) and tetrahydrofuran (100 g) under an ice-cooling condition, followed by 2 hours of agitation at room temperature after completion of the addition. The thus obtained reaction product was subjected to cation exchange, thereby obtaining a crude dipotassium salt. Furthermore, dipotassium salt of Compound No. 1 was reacted with tetraethyl ammonium chloride in a mixed solvent of acetonitrile and dimethoxyethane for ion exchange, to yield di(tetraethyl ammonium) salt of Compound No. 1 (1.85 g, 4.2 mmol).

Example 1-4 Synthesis of Dilithium Salt of Compound No. 2 ($1^{st}$ Production Process)

Tributylamine (3.5 g, 19 mmol) was slowly added dropwise to a flask containing fluorophosphoramide.tributylamine salt ($Bu_3NH[PO_2F(NH_2)]$) (2.8 g, 9.9 mmol), POFCl ($OCH_2CH=CH_2$)(1.9 g, 12.0 mmol) and acetonitrile (40 g) under an ice-cooling condition, followed by 2 hours of agitation at room temperature after completion of the addition. The thus obtained reaction product was subjected to cation exchange, thereby obtaining a crude dilithium salt. The resultant product was purified by reprecipitation using an acetonitrile solvent, to yield dilithium salt of Compound No. 2 (0.95 g, 4.1 mmol).

Example 1-5 Synthesis of Dilithium Salt of Compound No. 3 ($1^{st}$ Production Process)

Triethylamine (2.0 g, 20 mmol) was slowly added dropwise to a flask containing fluorophosphoramide.triethylamine salt ($Et_3NH[PO_2F(NH_2)]$) (2.0 g, 9.9 mmol), POFCl ($OCH_2C\equiv CH$) (1.7 g, 11 mmol) and tetrahydrofuran (30 g) under an ice-cooling condition, followed by 2 hours of agitation at room temperature after completion of the addition. The thus obtained reaction product was subjected to cation exchange, thereby obtaining a crude dilithium salt. The resultant product was purified by reprecipitation using an acetonitrile solvent, to yield dilithium salt of Compound No. 3 (1.5 g, 6.5 mmol).

Example 1-6 Synthesis of Dilithium Salt of Compound No. 4 ($2^{nd}$ Production Process)

Triethylamine (2.6 g, 26 mmol) was slowly added dropwise to a flask containing (3-butenyl)amidofluorophosphate ($H_2NPOF(OCH_2CH_2CH=CH_2)$) (2.0 g, 13 mmol), chlorofluorophosphoric acid triethylamine salt ($Et_3NH[PO_2FCl]$) (2.9 g, 13 mmol) and tetrahydrofuran (50 g) under an ice-cooling condition, followed by 20 hours of agitation at 50° C. after completion of the addition. The thus obtained reaction product was subjected to cation exchange, thereby obtaining a crude dilithium salt. The resultant product was purified by reprecipitation using an acetonitrile solvent, to yield dilithium salt of Compound No. 4 (1.2 g, 4.9 mmol).

Example 1-7 Synthesis of Dilithium Salt of Compound No. 5 ($1^{st}$ Production Process)

Lithium hydride (0.19 g, 24 mmol) was added to a flask containing fluorophosphoramide.lithium salt ($Li[PO_2F(NH_2)]$) (1.2 g, 11 mmol) $POF_2(OCH_2CF_3)$ (2.2 g, 12 mmol) and acetonitrile (100 g), followed by 2 hours of agitation at 50° C. The thus obtained reaction product was purified by reprecipitation using an acetonitrile solvent, to yield dilithium salt of Compound No. 5 (0.88 g, 3.2 mmol).

Example 1-8 Synthesis of Dilithium Salt of Compound No. 6 ($3^{rd}$ Production Process)

Sulfuryl fluoride ($SO_2F_2$) (1.5 g, 15 mmol) was slowly introduced into a 200-mL autoclave containing fluorophosphoramide.triethylamine salt ($Et_3NH[PO_2F(NH_2)]$) (2.0 g, 9.9 mmol), triethylamine (2.2 g, 22 mmol) and acetonitrile (40 g) under an ice-cooling condition. After completion of introduction, the resultant product was agitated for 2 hours at room temperature. The thus obtained reaction product was subjected to cation exchange, thereby obtaining a crude dilithium salt. The resultant product was purified by reprecipitation using a mixed solvent of acetonitrile and diethyl ether, to yield dilithium salt of Compound No. 6 (0.79 g, 4.1 mmol).

Example 1-9 Synthesis of Dilithium Salt of Compound No. 7 ($4^{th}$ Production Process)

Triethylamine (3.0 g, 30 mmol) was slowly added dropwise to a flask containing methyl sulfamate ($MeOSO_2NH_2$) (2.2 g, 20 mmol), lithium difluorophosphate ($LiPO_2F_2$) (1.5 g, 14 mmol), lithium chloride (1.2 g, 29 mmol) and tetrahydrofuran (50 g) under an ice-cooling condition, followed by 28 hours of agitation at 50° C. after completion of the addition. The thus obtained reaction product was purified by reprecipitation using an acetonitrile solvent, to yield dilithium salt of Compound No. 7 (0.61 g, 3.0 mmol).

Example 1-10 Synthesis of Dilithium Salt of Compound No. 8 ($4^{th}$ Production Process)

Lithium hydride (0.35 g, 44 mmol) was added to a flask containing (2-propenyl)sulfamate ($CH_2=CHCH_2OSO_2NH_2$) (3.0 g, 22 mmol), lithium chlorofluorophosphate ($LiPO_2FCl$) (2.5 g, 20 mmol) and tetrahydrofuran (70 g), followed by 10 hours of agitation at 50° C. The thus obtained reaction product was purified by reprecipitation using an acetonitrile solvent, to yield dilithium salt of Compound No. 8 (2.2 g, 9.5 mmol).

Example 1-11 Synthesis of Dilithium Salt of Compound No. 9 (3rd Production Process)

Triethylamine (2.2 g, 22 mmol) was slowly added dropwise to a flask containing fluorophosphoramide.triethylamine salt ($Et_3NH[PO_2F(NH_2)]$) (2.0 g, 9.9 mmol), ($CH\equiv CCH_2O)SO_2Cl$ (1.4 g, 9.1 mmol) and tetrahydrofuran (30 g) under an ice-cooling condition, followed by 2 hours of agitation at room temperature after completion of the addition. The thus obtained reaction product was subjected to cation exchange, thereby obtaining a crude dilithium salt. The resultant product was purified by reprecipitation using an acetonitrile solvent, to yield dilithium salt of Compound No. 9 (0.71 g, 3.1 mmol).

Example 1-12 Synthesis of Dilithium Salt of Compound No. 10 (4th Production Process)

Lithium hydride (0.17 g, 22 mmol) was added to a flask containing (2,2,2-trifluoroethyl)sulfamate ($CF_3CH_2OSO_2NH_2$) (2.2 g, 12 mmol) lithium chlorofluorophosphate ($LiPO_2FCl$) (1.2 g, 10 mmol) and tetrahydrofuran (50 g), followed by 10 hours of agitation at 50° C. The thus obtained reaction product was purified by reprecipitation using an acetonitrile solvent, to yield dilithium salt of Compound No. 10 (1.3 g, 5.0 mmol).

Example 1-13 Synthesis of Dilithium Salt of Compound No. 11 ($3^{rd}$ Production Process)

Triethylamine (1.2 g, 12 mmol) was slowly added dropwise to a flask containing fluorophosphoramide.triethylamine salt (Et₃NH [PO₂F(NH₂)]) (1.0 g, 5.0 mmol), (CF₃)₂CHOSO₂F (1.5 g, 6.0 mmol) and tetrahydrofuran (50 g) under an ice-cooling condition, followed by 2 hours of agitation at room temperature after completion of the addition. The thus obtained reaction product was subjected to cation exchange, thereby obtaining a crude dilithium salt. The resultant product was purified by reprecipitation using an acetonitrile solvent, to yield dilithium salt of Compound No. 11 (0.75 g, 2.2 mmol).

Example 2-1 Measurement of Ionic Conductance

The dilithium salt of Compound No. 1 obtained in Example 1-1 (1$^{st}$ production process) was dissolved in a mixed solvent (volumetric mixing ratio of 1:1) of ethylene carbonate and ethyl methyl carbonate, so as to prepare a 1 mmol/l solution, and then the ionic conductance of the resultant solution was measured at 30° C. using a conductivity meter (AC bipolar, HORIBA Ltd.). Table 1 shows the results.

Example 2-2 Measurement of Ionic Conductance

The dilithium salt of Compound No. 1 obtained in Example 1-2 (2$^{nd}$ production process) was dissolved in a mixed solvent (volumetric mixing ratio of 1:1) of ethylene carbonate and ethyl methyl carbonate, so as to prepare a 1 mmol/l solution, and then the ionic conductance of the resultant solution was measured at 30° C. using a conductivity meter (AC bipolar, HORIBA Ltd.). Table 1 shows the results. It was confirmed from the results of the above Examples 2-1 and 2-2 that no difference was observed in ionic conductances between these different processes.

Examples 2-3 to 2-13 Measurement of Ionic Conductance

The divalent imidic acid compounds obtained in Examples 1-3 to 1-13 were each dissolved as shown in Table 1 in a mixed solvent (volumetric mixing ratio of 1:1) of ethylene carbonate and ethyl methyl carbonate, so as to prepare 1 mmol/l solutions, and then the ionic conductances were measured at 30° C. using a conductivity meter (AC bipolar, HORIBA Ltd.). Table 1 shows the results.

Comparative Example 1

Bis(trifluoromethanesulfonyl)imide lithium was dissolved in a mixed solvent (volumetric mixing ratio of 1:1) of ethylene carbonate and ethyl methyl carbonate, so as to prepare a 1 mmol/l solution, and then the ionic conductance of the resultant solution was measured at 30° C. using a conductivity meter (AC bipolar, HORIBA Ltd.). Table 1 shows the results.

Comparative Example 2

Bis(difluorophosphoryl)imide lithium was dissolved in a mixed solvent (volumetric mixing ratio of 1:1) of ethylene carbonate and ethyl methyl carbonate, so as to prepare a 1 mmol/l solution, and then the ionic conductance of the resultant solution was measured at 30° C. using a conductivity meter (AC bipolar, HORIBA Ltd.). Table 1 shows the results.

TABLE 1

| | Compound | Production Process | Conductance [μS/cm] |
|---|---|---|---|
| Example 2-1 | Dilithium salt of Compound No. 1 | 1st production process (Example 1-1) | 48 |
| Example 2-2 | Dilithium salt of Compound No. 1 | 2nd production process (Example 1-2) | 48 |
| Example 2-3 | Ditetraethylammonium salt of Compound No. 1 | 1st production process (Example 1-3) | 41 |
| Example 2-4 | Dilithium salt of Compound No. 2 | 1st production process (Example 1-4) | 40 |
| Example 2-5 | Dilithium salt of Compound No. 3 | 1st production process (Example 1-5) | 39 |

TABLE 1-continued

| | Compound | Production Process | Conductance [μS/cm] |
|---|---|---|---|
| Example 2-6 | Dilithium salt of Compound No. 4 | 2nd production process (Example 1-6) | 37 |
| Example 2-7 | Dilithium salt of Compound No. 5 | 1st production process (Example 1-7) | 39 |
| Example 2-8 | Dilithium salt of Compound No. 6 | 3rd production process (Example 1-8) | 50 |
| Example 2-9 | Dilithium salt of Compound No. 7 | 4th production process (Example 1-9) | 47 |
| Example 2-10 | Dilithium salt of Compound No. 8 | 4th production process (Example 1-10) | 39 |
| Example 2-11 | Dilithium salt of Compound No. 9 | 3rd production process (Example 1-11) | 41 |
| Example 2-12 | Dilithium salt of Compound No. 10 | 4th production process (Example 1-12) | 45 |
| Example 2-13 | Dilithium salt of Compound No. 11 | 3rd production process (Example 1-13) | 46 |
| Comparative example 1 | Bis(trifluoromethanesulfonyl)imide lithium | — | 35 |
| Comparative example 2 | Bis(difluorophosphoryl)imide lithium | — | 36 |

The present divalent imidic acid compound provides an ionic conductance equivalent to or higher than that of bis(trifluoromethanesulfonyl)imide. This indicates that the present divalent imidic acid compound has anionic conductance equivalent to or higher than that of the conventionally known diimide compound having a perfluoroalkyl group, dimethide compound, and triimide compound.

Moreover, the present divalent imidic acid compound has a molecular weight lower than that of the conventional diimide compound having a perfluoroalkyl group, a dimethide compound, and a triimide compound. Hence, the present divalent imidic acid compound is clearly advantageous in view of the ratio of ionic conductance/molecular weight.

Furthermore, the present imidic acid compound is neither a diimidic acid compound having a perfluoroalkylsulfonyl group nor an imidic acid compound having a sulfonate group ($-SO_3^-$). Hence, the present imidic acid compound provides no risk of corroding aluminum as an electrode collector, when used for an electrolyte of an energy device.

What is claimed is:

1. A divalent imidic acid compound, which is represented by the following formula (1) or (2):

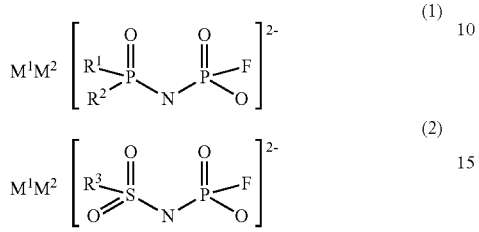

wherein in formulae (1) and (2), $R^1$ to $R^3$ each independently represent a fluorine atom or an organic group selected from the group consisting of a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group; and wherein $M^1$ and $M^2$ each independently represent a proton, a metal cation or an onium cation.

2. The imidic acid compound according to claim 1, wherein the $R^1$ to $R^3$ represent a fluorine atom or an organic group selected from the group consisting of a C1-10 alkoxy group, a C2-10 alkenyloxy group and a C2-10 alkynyloxy group.

3. The imidic acid compound according to claim 1, wherein the alkoxy group is selected from the group consisting of a methoxy group, an ethoxy group and a propoxy group; the alkenyloxy group is selected from the group consisting of a 1-propenyloxy group, a 2-propenyloxy group, a 2-butenyloxy group and a 3-butenyloxy group; and the alkynyloxy group is selected from the group consisting of a 2-propynyloxy group and a 1,1-dimethyl-2-propynyloxy group.

4. The imidic acid compound according to claim 1, wherein the $R^1$ to $R^3$ are all fluorine atoms.

5. The imidic acid compound according to claim 1, wherein, in the formula (1), $R^1$ represents a fluorine atom, and $R^2$ represents an organic group selected from the group consisting of a linear or branched C1-10 alkoxy group, a C2-10 alkenyloxy group, a C2-10 alkynyloxy group, a C3-10 cycloalkyloxy group, a C3-10 cycloalkenyloxy group and a C6-10 aryloxy group, and wherein a fluorine atom, an oxygen atom or an unsaturated bond may also be present in the organic group.

6. The imidic acid compound according to claim 1, wherein $M^1$ and $M^2$ in the formulae (1) and (2) each represent at least one cation selected from the group consisting of a proton, a lithium ion, a sodium ion, a potassium ion, a tetraalkylammonium ion and a tetraalkylphosphonium ion.

7. An electrolyte for an electrochemical device, comprising the imidic acid compound according to claim 1.

8. An antistatic agent, comprising the imidic acid compound according to claim 1.

9. A process for producing an imidic acid compound represented by the following formula (1),

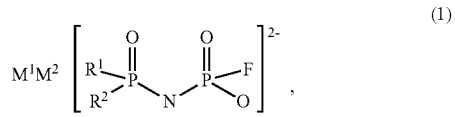

which comprises,
in the presence of an organic base or an inorganic base, reacting a fluorophosphoric amide salt of the formula $M^1[PO_2F(NH_2)]$ and/or $M^2[PO_2F(NH_2)]$, wherein $M^1$ and $M^2$ represent protons, metal cations or onium cations with
a halogenated phosphate of the formula $O=PR^1R^2X$, wherein X represents a halogen, and $R^1$ and $R^2$ each independently represent a fluorine atom or an organic group selected from the group consisting of a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, and wherein a fluorine atom, an oxygen atom or an unsaturated bond may also be present in the organic group,
wherein, in formula (1), $R^1$, $R^2$, $M^1$ and $M^2$ are each as defined above.

10. A process for producing an imidic acid compound represented by the following formula (1),

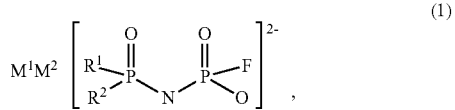

comprising,
in the presence of an organic base or an inorganic base, reacting a phosphoramide of the formula $O=PR^1R^2(NH_2)$, wherein $R^1$ and $R^2$ each independently represent a fluorine atom or an organic group selected from the group consisting of a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group, with
a fluorophosphate of the formula $M^1[PO_2FX]$ and/or $M^2[PO_2FX]$, wherein X represents a halogen, and $M^1$ and $M^2$ represent protons, metal cations or onium cations,
wherein, in formula (1), $R^1$, $R^2$, $M^1$ and $M^2$ are each as defined above.

11. A process for producing an imidic acid compound represented by the following formula (2),

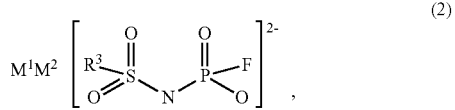

comprising,
in the presence of an organic base or an inorganic base, reacting a fluorophosphoric amide salt of the formula $M^1[PO_2F(NH_2)]$ and/or $M^2[PO_2F(NH_2)]$, wherein $M^1$ and $M^2$ represent protons, metal cations or onium cations with a sulfonyl halide of the formula $R^3SO_2X$, wherein X represents a halogen, and $R^3$ represents a fluorine atom or an organic group selected from the group consisting of a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, and wherein a fluorine atom, an oxygen atom or an unsaturated bond may also be present in the organic group, wherein, in formula (2), $R^3$, $M^1$ and $M^2$ are each as defined above.

12. A process for producing an imidic acid compound represented by the following formula (2),

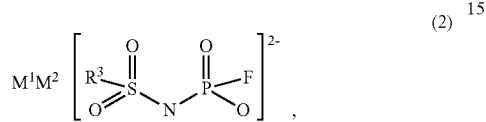
(2)

comprising, in the presence of an organic base or an inorganic base, reacting a sulfonyl amide of the formula $R^3SO_2NH_2$, wherein $R^3$ represents a fluorine atom or an organic group selected from the group consisting of a linear or branched C1-10 alkoxy group, a C2-10 alkenyloxy group, a C2-10 alkynyloxy group, a C3-10 cycloalkoxy group, a C3-10 cycloalkenyloxy group and a C6-10 aryloxy group, wherein a fluorine atom, an oxygen atom or an unsaturated bond may also be present in the organic group, with a fluorophosphate of the formula $M^1[PO_2FX]$ and/or $M^2[PO_2FX]$, wherein X represents a halogen, and $M^1$ and $M^2$ represent protons, metal cations or onium cations, wherein, in formula (2), $R^3$, $M^1$ and $M^2$ are each as defined above.

* * * * *